United States Patent [19]

Mrozik

[11] 4,423,209
[45] Dec. 27, 1983

[54] PROCESSES FOR THE INTERCONVERSION OF AVERMECTIN COMPOUNDS

[75] Inventor: Helmut H. Mrozik, Matawan, N.J.

[73] Assignee: Merck & Co., Inc., Rahway, N.J.

[21] Appl. No.: 352,666

[22] Filed: Feb. 26, 1982

[51] Int. Cl.$^3$ .................... C07H 17/08; C07D 313/00
[52] U.S. Cl. ...................................... 536/7.1; 549/264
[58] Field of Search .......................... 549/264; 536/7.1

[56] References Cited

U.S. PATENT DOCUMENTS

| | | | |
|---|---|---|---|
| 3,950,360 | 4/1976 | Aoki et al. | 260/343.2 |
| 4,156,720 | 5/1979 | Fisher et al. | 536/7.1 |
| 4,171,314 | 10/1979 | Chabala et al. | 549/264 |
| 4,173,571 | 11/1979 | Chabala et al. | 549/264 |
| 4,199,569 | 4/1980 | Chabala et al. | 424/180 |
| 4,206,205 | 6/1980 | Mrozik et al. | 424/180 |
| 4,289,760 | 9/1981 | Mrozik et al. | 536/7.1 |
| 4,310,519 | 1/1982 | Albers-Schonberg et al. | 424/181 |

OTHER PUBLICATIONS

Chabala et al., (IV), *Journal of Agricultural & Food Chemistry*, 29, 881, (1981).

*Primary Examiner*—Johnnie R. Brown
*Attorney, Agent, or Firm*—David L. Rose; Mario A. Monaco

[57] ABSTRACT

There is disclosed a process for converting avermectin compounds (formerly identified as C-076 compounds) of the A-type, into avermectin compounds of the B-type. The process is carried out on the naturally occurring avermectin compounds as well as on derivatives thereof. The process involves selectively cleaving the 5-methoxy group, converting it into the hydroxy group, through the intermediate 5-keto group.

4 Claims, No Drawings

PROCESSES FOR THE INTERCONVERSION OF AVERMECTIN COMPOUNDS

BACKGROUND OF THE INVENTION

The avermectin compounds are a series of compounds which are isolated from the fermentation broth of *Streptomyces avermitilis*. The morphological characteristics of the culture, as well as the fermentation methods and processes of isolation of the avermectin compounds is described in U.S. Pat. No. 4,310,519.

The avermectin compounds have the following structure:

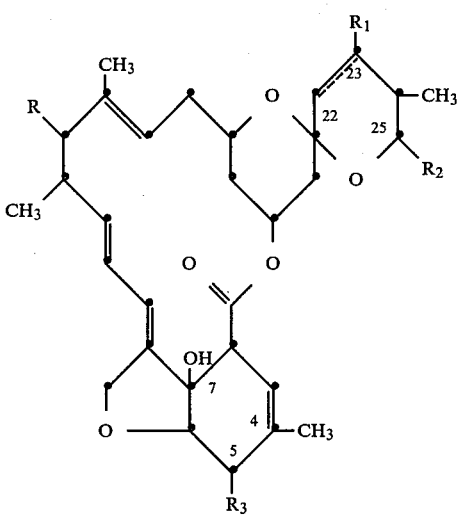

wherein

R is hydrogen, hydroxy, the 4'-($\alpha$-L-oleandrosyl)-$\alpha$-L-oleandrose group of the structure:

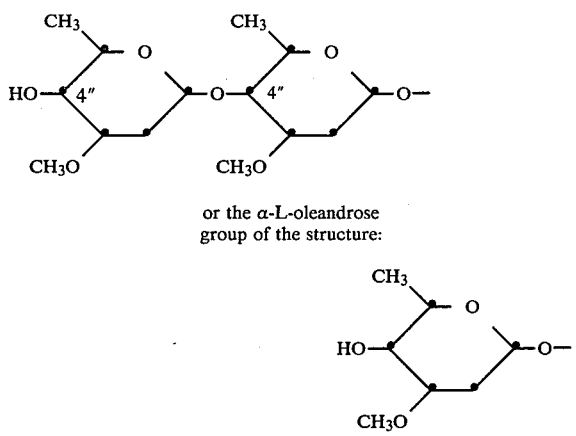

or the $\alpha$-L-oleandrose
group of the structure:

and wherein the broken line at the 22,23-position indicates a single or double bond provided that the double bond is present only when $R_2$ is iso-propyl or sec butyl;

$R_1$ is hydrogen or hydroxy and is present only when said broken line indicates a single bond;

$R_2$ is methyl, ethyl iso-propyl or sec-butyl; and $R_3$ is methoxy or hydroxy.

The compounds wherein $R_3$ is hydroxy are the compounds prepared by the process of this invention.

There are eight different avermectin natural product compounds and they are given the designations A1a, A1b, A2a, A2b, B1a, B1b, B2a, B2b, based upon the structure of the individual compounds.

With reference to the $R_1$, $R_2$ and $R_3$ groups of the above structural formula, the individual avermectin compounds, as described in U.S. Pat. No. 4,310,519, are as set forth below (the R group is 4'($\alpha$-L-oleandrosyl)-$\alpha$-L-oleandrose):

|  | $R_1$ | $R_2$ | $R_3$ |
| --- | --- | --- | --- |
| A1a | Double Bond | sec-butyl | —OCH$_3$ |
| A1b | Double Bond | iso-propyl | —OCH$_3$ |
| A2a | —OH | sec-butyl | —OCH$_3$ |
| A2b | —OH | iso-propyl | —OCH$_3$ |
| B1a | Double Bond | sec-butyl | —OH |
| B1b | Double Bond | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The compounds wherein $R_2$ is methyl or ethyl are disclosed in U.S. Pat. No. 3,950,360 to Aoki et al. and are identified as B-41 or milbemycin compounds. Such compounds have the same 16-membered macrocyclic ring as the avermectin compounds, however, the substitution pattern, particularly at the 13-, 22-, 23- and 25-positions are differrent. Those B-41 or milbemycin compounds with a 5-methoxy group have been found to be convertible to the 5-hydroxy compound using the process of this invention.

In addition, derivatives of the avermectin compounds have been prepared. In particular, the 22,23-dihydro derivatives of the 1-series of compounds have been found to have particularly advantageous biological properties. The 22,23-dihydro B1a/B1b derivatives are prepared by selectively hydrogenating the 22,23 unsaturated precursor. That is, such compounds are prepared from the avermectin B1a/B1b pair of compounds. The 22,23 dihydro compounds and their preparation are described in European published patent application Ser. No. 8300435.1. This, of course, requires that the avermectin B1a/B1b pair of compounds be separated from the A1a/A1b, A2a/A2b and B2a/B2b pairs of compounds, and then reduced to prepare the dihydro derivatives. The main problem encountered with this procedure is that the A1a/A1b, A2a/A2b and B2a/B2b compounds remain unused, and in effect wasted. In particular, it is desirable to convert the A compounds into the B compounds, since the B-compounds, with the 5-hydroxy group, have a higher level of antiparasitic activity than the A compounds.

The process of the instant invention reduces this waste by converting the unused A compounds into B compounds. The B compounds, particularly the B1a/B1b compounds, are preferred for their biological activity. Thus by converting unused A1a/A1b compounds into B1a/B1b compounds, additional precursors to the most preferred compounds are made available. Since such precursors are available only by fermentation techniques, no synthetic schemes being available, the increased yield of the preferred precursor represents a considerable savings.

SUMMARY OF THE INVENTION

The instant invention involves processes for the conversion of certain avermectin compounds into other avermectin compounds and derivatives. In particular, this invention involves processes for the conversion of avermectin A compounds into avermectin B compounds and derivatives thereof. Thus, it is an object of this invention to describe the processes for the conversion of such avermectin compounds into the preferred avermectin compounds and derivatives. It is a further object of this invention to describe the protecting groups and reactions therefor which facilitate the foregoing reactions. Further objects will become apparent from reading the following description.

DESCRIPTION OF THE INVENTION

As mentioned above, the instant process achieves the conversion of the avermectin A compounds into the preferred avermectin B compounds.

As is noted from the foregoing structure, the A compounds have a methoxy group at the 5-position and the B compounds have a hydroxy group at the 5-position. The conversion of the avermectin A compounds into the avermectin B compounds thus involves the conversion of the 5-methoxy group into the 5-hydroxy group.

While there are many procedures known in the art for the removal of a methyl from a methoxy group and the replacement thereof by a hydrogen, (that is, the cleavage of an ether bond) an analysis of the avermectin molecule will reveal that there are 8 ether bonds present in addition to the 5-methoxy which could be cleaved by conventional procedures. Thus a reagent or procedure which merely cleaved ether bonds would utterly destroy the molecule. In addition, of the 8 additional ether bonds, 2 are methoxy groups (at the 3' and 3" positions), which is the same ether group as is at the 5-position. Thus the procedure which converts avermectin A compounds into B compounds must be very selective.

The procedure employed for the selective cleavage of the 5-methoxy group and conversion thereof into the 5-hydroxy group is best exemplified in the following reaction scheme:

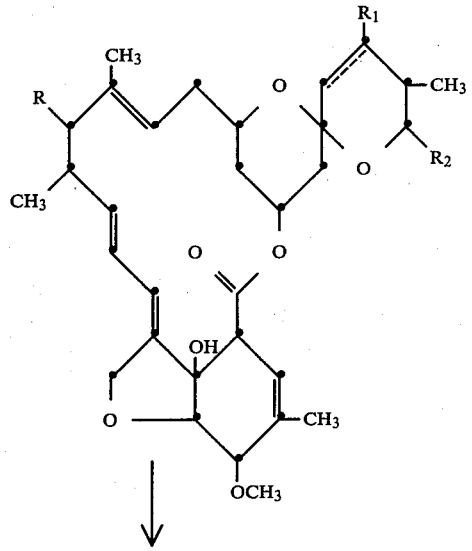

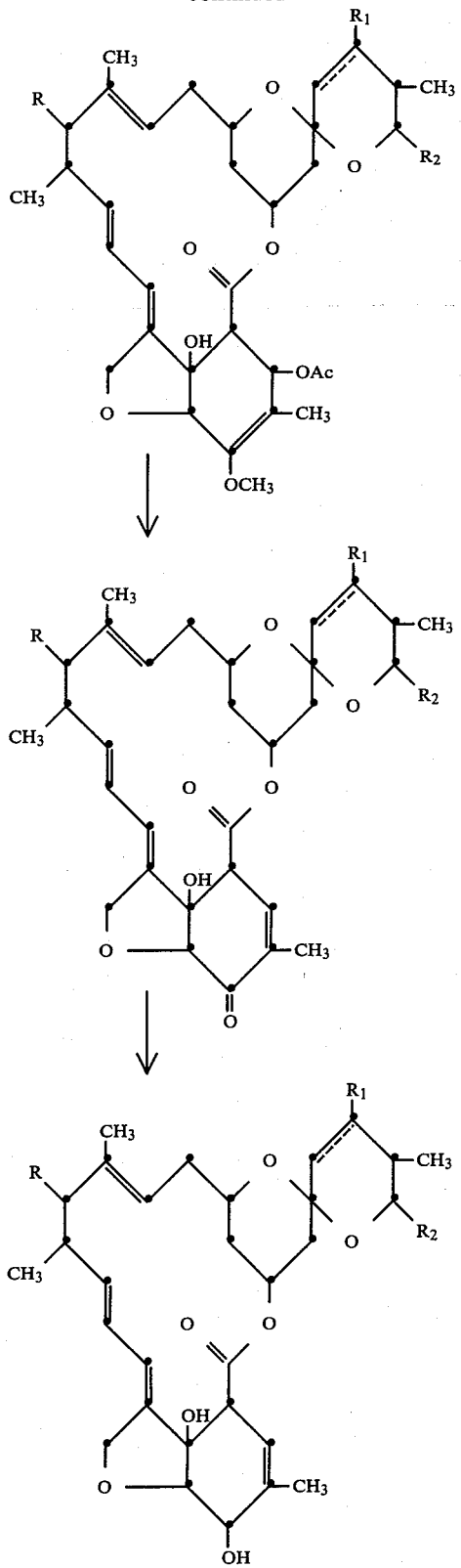

wherein
the broken line indicates a single or a double bond, at the 22,23-position provided that the double bond is present only when $R_2$ is iso-propyl or sec-butyl;

R$_1$ is hydrogen or hydroxy, provided R$_1$ is hydroxy only when the broken line indicates a single bond;
R$_2$ is methyl, ethyl, sec-butyl or isopropyl;
R$_3$ is hydrogen, hydroxy,

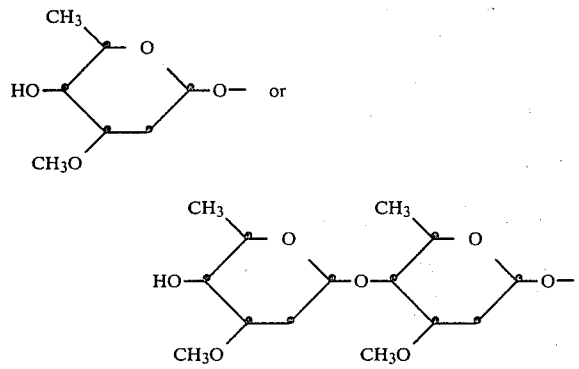

and Ac is acetyl.

In the first step of the foregoing reaction scheme, an avermectin A compound or derivative thereof, suitably protected, is treated with mercuric acetate. The reaction is carried out in an inert solvent such as toluene, methylenechloride, tetrahydrofuran, N,N-dimethylformamide and the like. Toluene is the preferred solvent. The reaction mixture is generally maintained at from 15° to 150° C. for from 15 minutes to 8 hours. Preferably the reaction is kept at about 105°–115° C. and at this temperature range the reaction is generally complete in from 2 to 4 hours. This first step produces a 3-acetoxy enol ether intermediate which, while it is stable and may be isolated, is generally hydrolyzed in situ with the simultaneous elimination of the 3-acetoxy group, to the 5-ketone. The hydrolysis is carried out using mild acidic hydrolysis conditions. The use of strong acid is to be avoided since other parts of the molecule, such as the sugar moieties, may be affected. The preferred hydrolysis medium is oxalic acid, or p-toluene sulfonic acid in the original reaction solvent system, or in a different solvent system, such as a loweralkanol, preferably methanol. The hydrolysis, using p-toluene sulfonic acid in methanol, is generally complete in from 5 minutes to 2 hours at from −10° to 25° C. It is preferred to carry out the reaction at about 15° C. The product is isolated using techniques known to those skilled in the art.

The 5-keto compound is then reduced to prepare the desired 5-hydroxy compound. (See. J. Agric. Food 29 881 (1981). The reduction is carried out using reducing agents such as sodium borohydride, tri-t-butoxyaluminum hydride, lithium aluminum hydride, and the like. The reaction is carried out in a solvent such as methanol, ethanol, ether, and the like, at temperatures of from −10° to 25° C., preferably from 0° to 15° C. Under such conditions the reaction is generally complete in from 10 minutes to 3 hours.

The starting material may be the original avermectin A compounds (containing the 5-methoxy substituent) which are disclosed in U.S. Pat. No. 4,310,519. In addition, the aforementioned Aoki et al. U.S. Pat. No. 3,950,360 discloses the B-41 or milbemycin compounds. In addition, derivatives of the avermectin and milbemycin compounds can be transformed from the 5-methoxy to the 5-hydroxy configuration using this process. The 22,23-dihydro compounds disclosed in U.S. Pat. No. 4,199,569; the monosaccharide and aglycone compounds of U.S. Pat. No. 4,206,205; the 13-deoxy compounds of U.S. Pat. Nos. 4,171,571 and 4,171,314 are all suitable for use in the instant conversion reaction. The foregoing references also describe the use of certain protecting groups which are suitable for protecting the substituent groups which are more vulnerable to side reactions.

The instant avermectin compounds are generally isolated as mixtures of the a and b compounds; that is, mixtures of compounds wherein the 25-position substituent is sec-butyl or isopropyl. Because the compounds are so closely related and have very similar physical properties they are very difficult to separate. Because the compounds have very similar biological properties, they are generally not separated. Thus when reference is made to an "a" compound, it generally contains a certain percentage of the "b" compound. The a compound is the one prepared in greater quantity generally constituting from 80 to 99% of the mixture. Likewise, even when the minor component ("b") is isolated it still contains a small amount of the major component.

In the instant application the nomenclature used to represent such mixtures is with a slash (/) between the compounds, such as B1a/B1b, or referring to the compounds without the a or b notation such as B1 or B2. Reference to compounds with only a small amount of the other component will be referred to as the major component such as in B1a or B1b.

The compounds prepared by the processes of this invention, as well as the compounds from which they are prepared, are very active antiparasitic agents. They are, in particular, very useful as anthelmintics, ectoparasiticides, insecticides and acaricides, in human and animal health and in agriculture. When used in human and animal therapy, the compounds may be administered orally, in a solid or liquid formulation, as a unit dosage formulation or in the food or feed of the animal; or the compound may be administered as an injectable liquid solution of suspension. Dosages of from 0.025 to 0.5 mg. per kg. of animal body weight are effective. In agricultural uses, the compounds may be administered as a liquid spray or a solid dust to be applied to the plants or the soil in which they are growing; or they may be applied to the crops in bulk storage or as they are packaged or processed.

The following examples are provided in order to understand and demonstrate the processes of the instant invention. The examples should not be construed as limitative of the instant invention.

EXAMPLE 1

5-Keto Avermectin B2a/B2b

100 Milligrams of avermectin A2a/A2b (0.11 mmole) was dissolved in 1.5 ml of toluene, and 100 Mg of mercuric acetate (0.32 mmole) was added and the reaction mixture stirred in an oil bath maintained at from 105° to 115° C. for 2½ hours. The reaction vessel was removed from the oil bath and allowed to cool to room temperature. The reaction mixture was diluted with ether and centrifuged. The insoluble white residue was removed and washed again with ether. The combined ether extracts were evaporated to dryness in vacuo to a yellow glass. This material was dissolved in 1 ml of methylene chloride and placed on three preparative layer (1000μ) silica gel chromatography plates and developed with 5% methanol in methylene chloride. Two bands of product were observed consisting of a 49 mg fraction and a 25 mg fraction. The 25 mg fraction was the product 5-keto avermectin B2a/B2b. The 49 mg fraction was the 3-O-acetyl-Δ-4,5-enol ether which was hydrolyzed as described below. One mg of the 49 mg enol ether fraction was dissolved in 0.15 ml tetrahydrofuran and 0.75 of methanol. 0.15 Milliliters of an aqueous solution of 150 mg of oxalic acid and 1.5 ml of water was added and the reaction mixture stirred at room temperature for 6 hours. The reaction mixture was added to a solution of aqueous sodium bicarbonate and ether and the ether layer was washed with water and dried over magnesium sulfate. The ether layer is evaporated to dryness affording about 1 mg of 5-keto avermectin B2a/B2b.

Alternatively, the enol ether was hydrolyzed by dissolving one mg in one ml of 0.1% p-toluene sulfonic acid hydrate dissolved in methanol and stirred at room temperature for from 30 to 60 minutes. A thin layer chromatography of the reaction mixture indicated that the starting material had all been converted to the 5-keto avermectin B2a/B2b. The structure was confirmed by comparing the 300 MHz nuclear magnetic resonance spectrum, mass spectrum and high pressure liquid chromatogram of the product with that of an authentic sample.

EXAMPLE 2

13,23 Di-O-acetyl 5-keto Avermectin B2a/B2b aglycone

50 Milligrams of 13,23 di-O-acetyl avermectin A2a/A2b aglycone was stirred in 0.75 ml of toluene under a blanket of nitrogen gas. 25 Milligrams of mercuric acetate was added and the reaction mixture heated in an oil bath at from 105° to 115° C. for 2 hours. The reaction mixture was cooled in an ice bath, diluted with about 7 ml of ether and the layers separated. The ether soluble portion was washed with dilute aqueous hydrochloric acid, sodium bicarbonate and water, and dried under a stream of nitrogen which afforded 55 mg of a yellow glass. This material was put on a preparative layer silica gel chromatography plate (1000μ) and developed with methylene chloride/ethyl acetate in proportions of 9:1. The band with an Rf of about 0.25 was removed from the silica gel affording 15.3 mg of a yellow oil which was confirmed by nuclear magnetic resonance spectroscopy as 13,23 O-diacetyl 5-keto avermectin B2a/B2b aglycon.

EXAMPLE 3

Avermectin-B2a/B2b

A solution of 90 mg (0.1 mmol) of 5-keto avermectin-B2a/B2b in 2 ml of EtOH was cooled to −15° C. and treated with 4.0 mg (0.106 mmol) sodium borohydride. After 15 min. the reaction mixture was quenched by addition of 10 ml of 0.1 N acetic acid, stirred 30 min., filtered, and washed. The filtrates were concentrated in vacuo to a solid residue. This was purified by preparative silica gel thin layer chromatography with a 87:13 (v/v) mixture of chloroform-tetrahydrofuran and provided 23.5 mg of pure avermectin B2a/B2b.

| Example | Starting Material | Intermediate | Product |
|---|---|---|---|
| 4 | avermectin A2b | 5-keto avermectin B2b | avermectin B2b |
| 5 | avermectin A1a | 5-keto avermectin B1a | avermectin B1a |
| 6 | avermectin A1b | 5-keto avermectin B1b | avermectin B1b |
| 7 | 22,23-dihydro avermectin A1a | 5-keto-22,23-dihydro avermectin B1a | 22,23-dihydro avermectin B1a |
| 8 | avermectin A2a monosaccharide | 5-keto-avermectin B2a monosaccharide | avermectin B2a monosaccharide |
| 9 | avermectin A2a aglycone | 5-keto avermectin B2a aglycone | avermectin B2a aglycone |
| 10 | 13-deoxy avermectin A2a aglycone | 5-keto 13-deoxyavermectin B2a aglycone | 13-deoxy avermectin B2a aglycone |
| 11 | 13-deoxy-22,23-dihydro avermectin A1b aglycone | 5-keto-13-deoxy-22,23-dihydro avermectin B1b aglycone | 13-deoxy-22,23-dihydro avermectin B1b aglycone |
| 12 | 13-deoxy-22,23-dihydro avermectin A1a aglycone | 5-keto-13-deoxy-22,23-dihydro avermectin B1a aglycone | 13-deoxy-22,23-dihydro avermectin B1a aglycone |
| 13 | milbemycin $\alpha_2$ | 5-keto milbemycin $\alpha_2$ | milbemycin $\alpha_1$ |
| 14 | milbemycin $\alpha_4$ | 5-keto milbemycin $\alpha_4$ | milbemycin $\alpha_3$ |

If the starting materials listed in Examples 4 to 14 are reacted as described in Example 1, the intermediate 5-keto compounds are obtained which, if reduced as described in Example 3, yields the named 5-hydroxy product.

What is claimed is:

1. A process for the preparation of a compound having the formula:

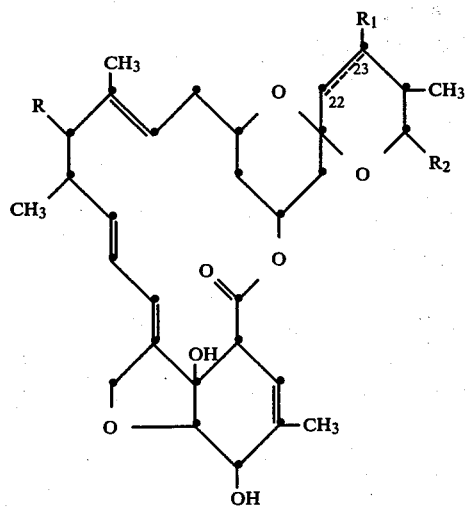

wherein
the broken line at the 22,23-position indicates a single or a double bond, provided that the double bond is present only when $R_2$ is iso-propyl or sec-butyl;
$R_1$ is hydrogen or hydroxy, provided $R_1$ is hydroxy only when the broken line indicates a single bond;
$R_2$ is methyl, ethyl, sec-butyl or isopropyl; and
R is hydrogen, hydroxy.

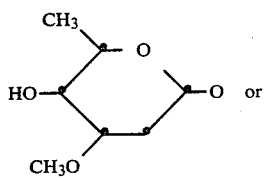

or

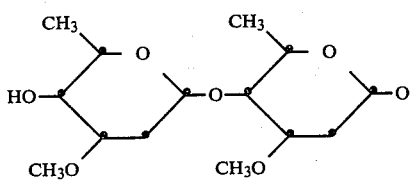

which comprises treating a compound having the formula:

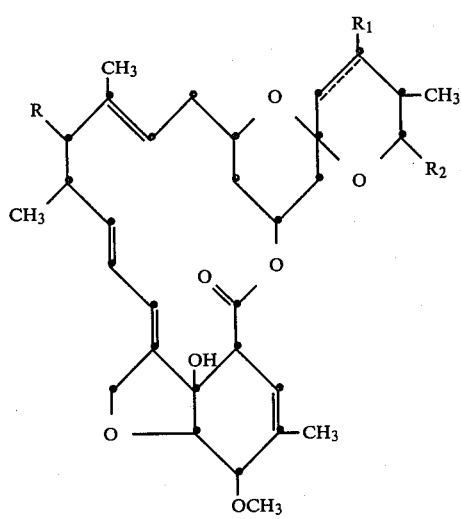

wherein R, $R_1$ and $R_2$ are as previously defined, with mercuric acetate and hydrolyzing the thus produced 3-acetoxy enol ether with a mild acid to produce a 5-keto compound having the formula:

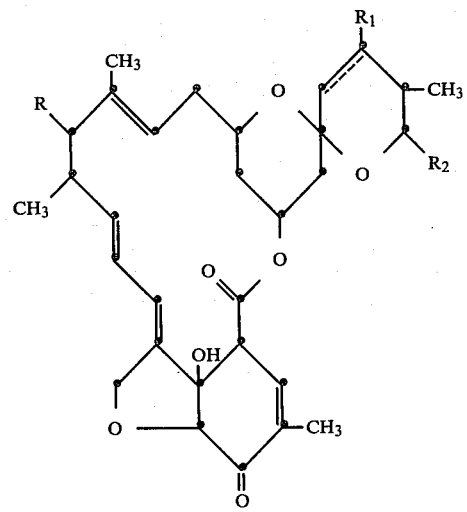

which is reduced with sodium borohydride, tri-t-butoxy aluminum hydride or lithium aluminum hydride to produce the desired compound.

2. The process of claim 1 wherein the hydrolysis step is carried out using oxalic acid or p-toluene sulfonic acid, and the reduction step is carried out using sodium borohydride.

3. The process of claim 2 wherein the mercuric acetate step is carried out at from 15° to 150° C. in an inert solvent; the hydrolysis step is carried out at from −10° to 25° C. in an inert solvent; and the reduction step is carried out at from −10° to 25° C. in an inert solvent.

4. The process of claim 3 wherein the mercuric acetate step is carried out at from 40°–115° C. in toluene, methylene chloride, tetrahydrofuran, or N,N-dimethylformamide; the hydrolysis step is carried out at about 15° C. in a lower alkanol; and the reduction step is carried out at from −15° to 15° C. in methanol, ethanol, or ether.

* * * * *